United States Patent
Ringermacher et al.

(10) Patent No.: US 7,516,663 B2
(45) Date of Patent: Apr. 14, 2009

(54) SYSTEMS AND METHOD FOR LOCATING FAILURE EVENTS IN SAMPLES UNDER LOAD

(75) Inventors: Harry Israel Ringermacher, Delanson, NY (US); Donald Robert Howard, Troy, NY (US); Bryon Edward Knight, Charlton, NY (US); Yury Alexeyevich Plotnikov, Niskayuna, NY (US); Mark John Osterlitz, Schenectady, NY (US); Jian Li, Schenectady, NY (US); Jeffry Lynn Thompson, Ballston Spa, NY (US); Gulperi Nuzhet Aksel, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 203 days.

(21) Appl. No.: 11/592,549

(22) Filed: Nov. 3, 2006

(65) Prior Publication Data
US 2008/0105055 A1  May 8, 2008

(51) Int. Cl.
*G01N 29/04* (2006.01)
*G01N 25/72* (2006.01)

(52) U.S. Cl. ............... 73/601; 73/587; 374/5; 250/341.6

(58) Field of Classification Search ............ 73/587, 73/601, 801; 250/341.6; 374/5
See application file for complete search history.

(56) References Cited

U.S. PATENT DOCUMENTS

| | | | |
|---|---|---|---|
| 4,269,065 A * | 5/1981 | Clark | 73/587 |
| 4,562,736 A | 1/1986 | Iwasaki et al. | |
| 5,069,005 A * | 12/1991 | Hovland et al. | 451/53 |
| 5,711,603 A | 1/1998 | Ringermacher et al. | |
| 6,367,968 B1 | 4/2002 | Ringermacher et al. | |
| 6,367,969 B1 | 4/2002 | Ringermacher et al. | |
| 6,394,646 B1 | 5/2002 | Ringermacher et al. | |
| 6,998,616 B2 * | 2/2006 | Favro et al. | 250/341.6 |
| 7,060,971 B2 * | 6/2006 | Zombo et al. | 250/252.1 |
| 2002/0141632 A1 | 10/2002 | Engelbart et al. | |
| 2004/0119019 A1 | 6/2004 | Thompson et al. | |
| 2005/0018745 A1 | 1/2005 | Lee | |

FOREIGN PATENT DOCUMENTS

| | | |
|---|---|---|
| EP | 1158296 | 11/2001 |
| EP | 1475629 | 11/2004 |

OTHER PUBLICATIONS

R. Graue et al., "Integrated Health Monitoring Approach for Reusable Cryogenic Tank Structures," Journal of Spacecraft and Rockets, American Institute of Aeronautics and Astronautics, vol. 37, No. 5, Sep. 2000 pp. 580-585.
EP Search Report, EP07119838, Jan. 15, 2008.

* cited by examiner

*Primary Examiner*—John E Chapman
(74) *Attorney, Agent, or Firm*—Penny A. Clarke

(57) ABSTRACT

A system for locating a failure event in a sample is disclosed. The system includes at least one sensor configured to detect acoustic energy corresponding to the failure event in the sample. The system also includes an infrared camera configured to detect a thermal release of energy corresponding to the failure event in the sample.

20 Claims, 6 Drawing Sheets

SYSTEMS AND METHOD FOR LOCATING FAILURE EVENTS IN SAMPLES UNDER LOAD

BACKGROUND

The invention relates generally to inspection technology and more specifically, to nondestructive testing techniques using thermography.

Composite structures are being increasingly used in aerospace and other applications. A variety of materials and manufacturing techniques can be employed, depending on the application. Benefits of composite structures include lower weight and increased strength. However, composite materials can exhibit a number of defect types, such as delaminations, matrix cracks and fiber breaks. In order to design improved composite structures and validate structural models, it would be desirable to determine both the source depth and actual location of failure events.

Infrared (IR) thermography is a technique for detecting and quantifying material defects and subsurface damage of objects. The technique relies upon temporal measurements of heat transference through the object to provide information concerning defects or cracks in the object. Since heat flow through the object is substantially unaffected by the microstructure of a material of the object, the technique is free of any constraints the microstructure might impose. Further, thermographic analysis is not significantly hampered by size, shape or contour of the object being tested. The technique may also be accomplished ten to one hundred times faster than existing conventional non-destructive testing techniques.

However, existing advanced thermographic imaging methods, utilizing transient flash methods, capable of locating the position of flaws in composites, as discussed in U.S. Pat. No. 6,367,969, Ringermacher et al, locate flaws after their creation and thus cannot assign a causal sequence to events creating these flaws. Causal sequences are desirable to obtain in order to validate computer models of failure in structures undergoing dynamic loading. Furthermore, it is desirable to find a precise location in terms of depth and lateral position of events, as well as sequence of events.

Hence, there is need for an improved thermographic technique that addresses the aforementioned issues.

BRIEF DESCRIPTION

In accordance with one embodiment, a system for locating a failure event in a sample is provided. The system includes at least one sensor configured to detect acoustic energy corresponding to the failure event in the sample. The system also includes an infrared camera configured to detect a thermal release of energy corresponding to the failure event in the sample.

In accordance with another embodiment of the invention, a method of detecting a failure event in a sample is provided. The method includes recording acoustic signals corresponding to the failure event. The method also includes determining a zero time based upon the acoustic signals. The method further includes recording a number of thermal images of the sample over a period of time. The method also includes determining a depth of the failure event from the acoustic signals and the thermal images.

In accordance with another embodiment of the invention, a multi-modal system for locating a failure event in a sample is provided. The system includes at least one sensor configured to detect acoustic energy corresponding to the failure event in the sample. The system also includes an infrared camera configured to detect a thermal release of energy corresponding to the failure event in the sample. The system further includes an X-ray source configured to irradiate at least a portion of the sample. The system also includes a digital X-ray detector configured to capture at least one X-ray image of at least a portion of the sample.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the present invention include a system for locating failure events in a sample under load and a method for locating the same. As used herein, the term "location" refers to position of the failure event underneath a surface of the sample. The term "load" refers to stress experienced by a sample being tested when placed in a load testing machine. The system disclosed herein includes a combination of infrared imaging and acoustic emission sensing in order to determine an initial time of occurrence of the failure event in the sample.

Figure 1:
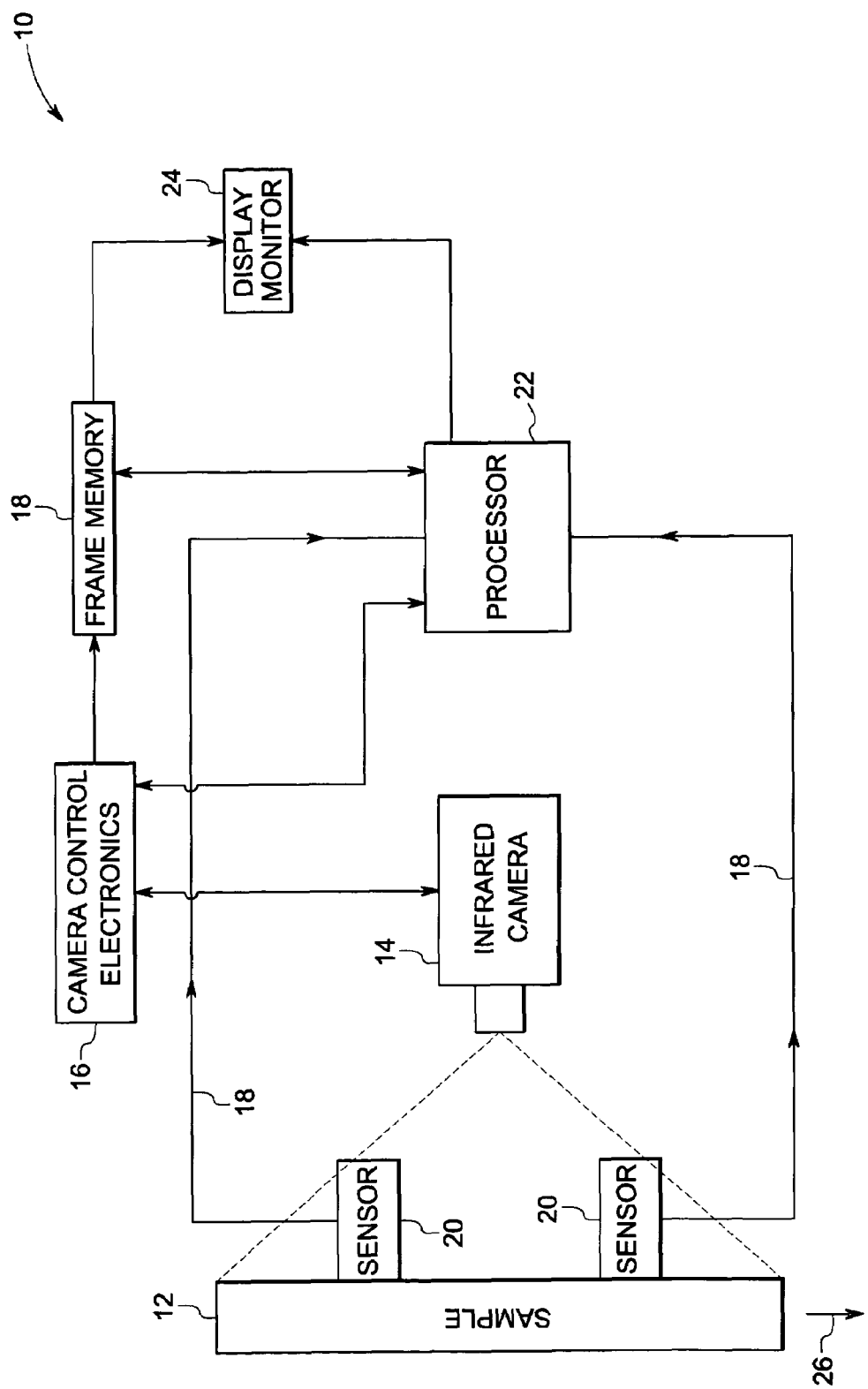
FIG. 1 is a diagrammatic illustration of a system for locating a failure event in a sample in accordance with embodiments of the invention.

FIG. 1 is a diagrammatic illustration of a system 10 for locating a failure event in a sample 12. The system 10 includes an infrared camera 14 configured to detect a thermal release of energy corresponding to the failure event in the sample 12. A non-limiting example of an infrared camera includes a focal plane array of sensors. The infrared camera 14 may be operated by a camera control electronics 16. The infrared camera 14 may also be configured to output thermal image data to the camera control electronics 16. In a particular embodiment, the infrared camera 14 records the thermal release of energy in multiple frames that is recorded in a frame memory 18. In a non-limiting example, the infrared camera 14 is configured to operate at a frame rate within a range of about 50 frames per second to about 250 frames per second. The system 10 includes at least one sensor 20 configured to detect acoustic energy corresponding to the failure event in the sample 12. In the illustrated example, the system 10 includes two sensors. In a particular embodiment, the sensor 20 may be mounted on a top surface of the sample 12. A non-limiting example of the sensor 20 is a transducer. The sensor 20 is configured to detect a zero-time event. As used herein, the term "zero-time" refers to a start time for occurrence of a failure event. When the failure event occurs deep inside the sample 12, the failure event releases a pulse of acoustic energy and thermal energy. The acoustic energy travels essentially at an infinite speed as compared to that of the thermal energy traveling towards a surface of the sample. Hence, detection of acoustic energy defines the zero time of the failure event.

The sensor 20 outputs data corresponding to the acoustic energy detected to a processor 22. The processor 22 also controls camera control electronics 16 and the frame memory 18 to acquire a pre-determined number of successive thermal image frames of the sample 12 that are stored in the frame memory 18. In one example, the processor is a microprocessor. The processor 22 is configured to output data such as a surface thermal profile of the sample 12 or an acoustic emission profile to a display monitor 24. The frame memory 18 may also output thermal image frames to the display monitor 24. In a particular embodiment, the sensor 20 and the infrared camera 14 are synchronized on a common time base. The processor 22 is configured to synchronize an acoustic emission event time detected by the sensor 20 with a respective one of the frames recorded by the infrared camera 14. In a particular embodiment, the sample 12 includes multiple plies oriented at angles in a range of about 0 degree to 180 degrees with respect to a longitudinal axis 26 of the sample. The longitudinal axis 26 of the sample may also be referred to as axis of stress in the sample 12.

Examples of failure events for composites include point events, line events and plane events. As used herein, "point event" refers to an instantaneous release of energy at a single point at a specific depth of the sample 12. A non-limiting example of a point event includes a snap of a fiber. The term "line event" refers to an instantaneous release of energy along a line at a specific depth of the sample 12. A non-limiting example of a line event includes a crack of an epoxy matrix along a line. The term "plane event" refers to an instantaneous release of energy along a plane at a specific depth of the sample 12. A non-limiting example of a plane event includes delamination of an epoxy matrix in a plane.

Figure 2:
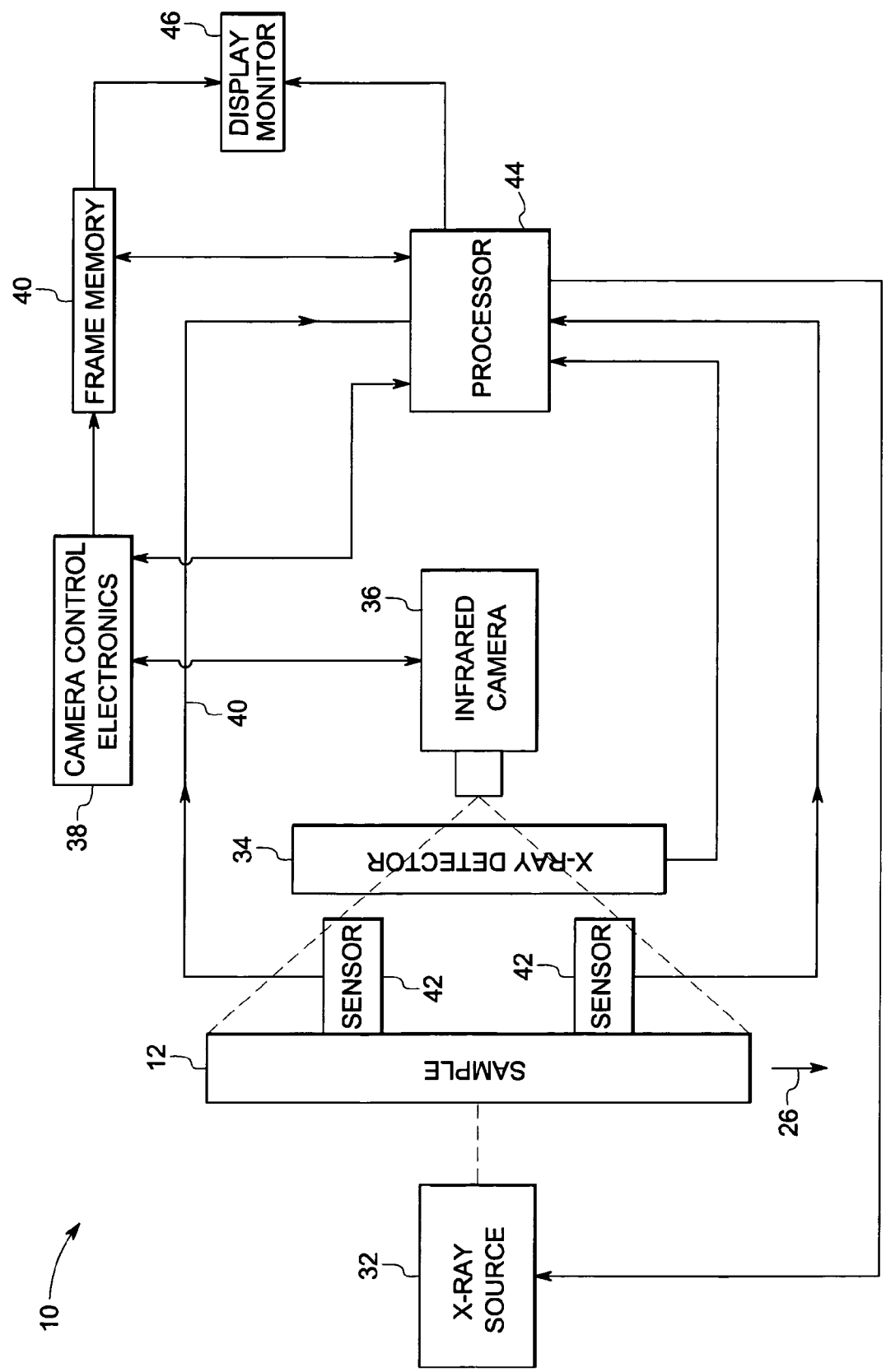
FIG. 2 is a diagrammatic illustration of an alternative system for locating a failure event in a sample including X-ray imaging in accordance with embodiments of the invention.

In another illustrated embodiment of the invention as shown in FIG. 2, an exemplary system 30 for locating a failure event in a sample 12 as referenced in FIG. 1 is depicted. The system 30 includes an X-ray source 32 and an X-ray detector 34 configured to capture an X-ray image of the sample 12. The system 30 also includes an infrared camera 36 configured to detect a thermal release of energy corresponding to the failure event in the sample 12. A non-limiting example of the infrared camera 36 includes a focal plane array of sensors. The infrared camera 36 may be operated by camera control electronics 38. The infrared camera 36 may also be configured to output thermal image data to the camera control electronics 38. In a particular embodiment, the infrared camera 36 records the thermal release of energy in multiple frames that is recorded in a frame memory 40. In a non-limiting example, the infrared camera 36 is configured to operate at a frame rate within a range of about 50 frames per second to about 250 frames per second. The X-ray detector 34 is configured to slide out of view of the infrared camera 36 when the thermal release of energy is being recorded. The system 30 further includes at least one sensor 42 configured to detect acoustic energy corresponding to the failure event in the sample 12. In the illustrated example, the system 30 includes two sensors. In a particular embodiment, the sensor 42 may be mounted on a top surface of the sample 12. A non-limiting example of the sensor 42 includes a transducer. The sensor 42 is configured to detect a zero-time of the failure event.

The sensor 42 outputs data corresponding to the acoustic energy detected to a processor 44. The processor 44 also controls camera control electronics 38 and the frame memory 40 to acquire a pre-determined number of successive thermal image frames of the sample 12 that are stored in the frame memory 40. The processor 44 may also control operation of the X-ray source 32. In one example, the processor is a microprocessor. The X-ray detector 34 also outputs data such as an X-ray image of the sample to the processor 44. The processor 44 is configured to output data to a display monitor 46. Some non-limiting examples of the data include a surface thermal profile, an acoustic emission profile or an X-ray image of the sample 12. The frame memory 40 may also output thermal image frames to the display monitor 46. In a particular embodiment, the sensor 42 and the infrared camera 36 are synchronized on a common time base. The processor 44 is configured to synchronize an acoustic emission event time detected by the sensor 42 with a respective one of the frames recorded by the infrared camera 36. The processor 44 is also configured to correlate the X-ray image with at least one of the multiple acoustic data obtained with the sensor 42 and multiple thermal data obtained with the infrared camera 36. In a particular embodiment, the sample 12 includes multiple plies oriented at angles in a range of about 0 degree to 180 degrees with respect to a longitudinal axis 26 as referenced in FIG. 1 of the sample 12. The longitudinal axis 26 of the sample 12 may also be referred to as an axis of stress in the sample 12. Some non-limiting examples of the failure event include a point event, a line event and a plane event. As noted above, one example of a point event is a fiber snap. One example of a line event is a crack of an epoxy matrix along a line. One example of a plane event is a delamination of an epoxy matrix in a plane.

Figure 3:
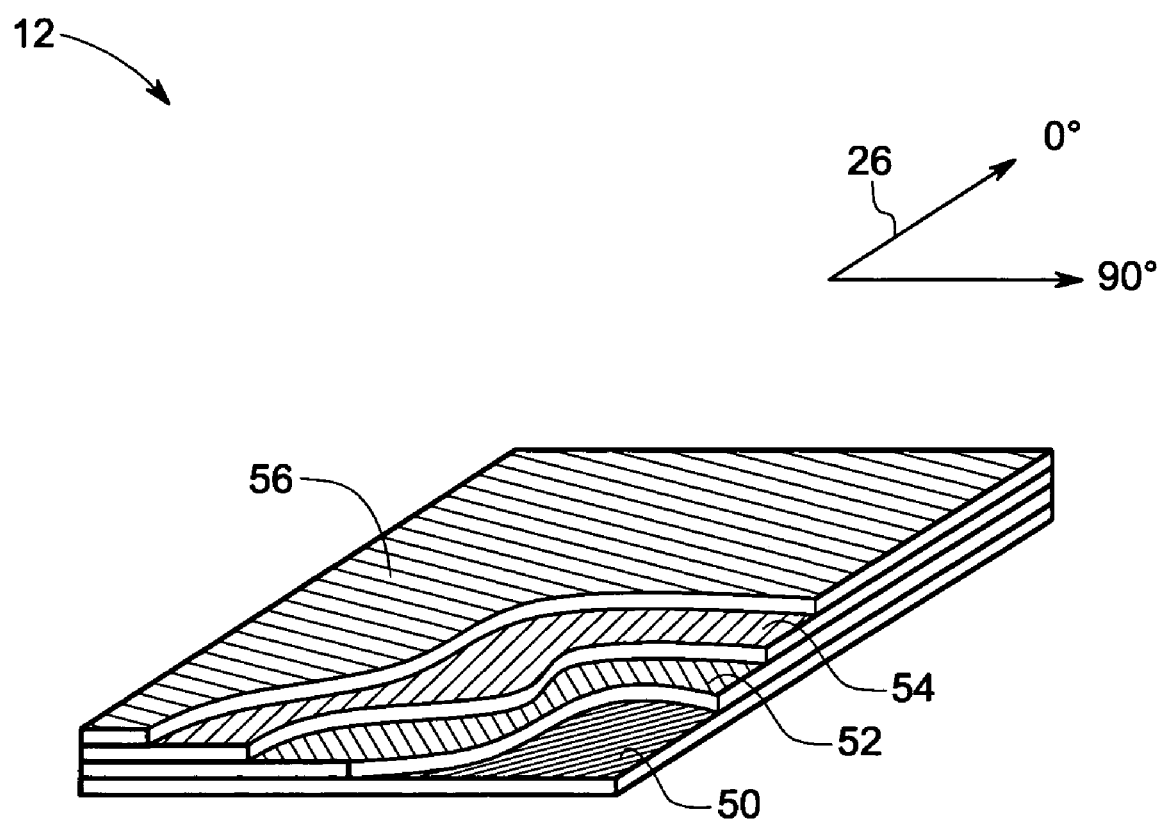
FIG. 3 is a schematic representation of a composite sample to be inspected for a failure event.

FIG. 3 is a diagrammatic illustration of an exemplary composite sample 12 as referenced in FIG. 1 and FIG. 2. In a particular embodiment, the sample 12 includes a layer 50 of ply oriented along a longitudinal axis 26 as referenced in FIG. 1 of the sample 12. The layer 50 may also be referred to as a zero degree ply. The zero degree ply forms a bottom surface of the sample 12. A layer 52 oriented at −45 degrees in an anticlockwise direction or 135 degrees in a clockwise direction with respect to the longitudinal axis 26 is disposed upon the zero degree ply 50. The layer 52 may also be referred to as a −45 degree ply. Further, a layer 54 oriented at an angle of 90 degrees with respect to the longitudinal axis 26 is disposed upon the −45 degree ply 52. The layer 54 may be referred to as a 90 degree ply. A layer 56 oriented at an angle of 45 degrees with respect to the longitudinal axis 26 may be disposed upon the 90 degree ply 54. The layer 56 may be referred to as a 45 degree ply.

Figure 4:
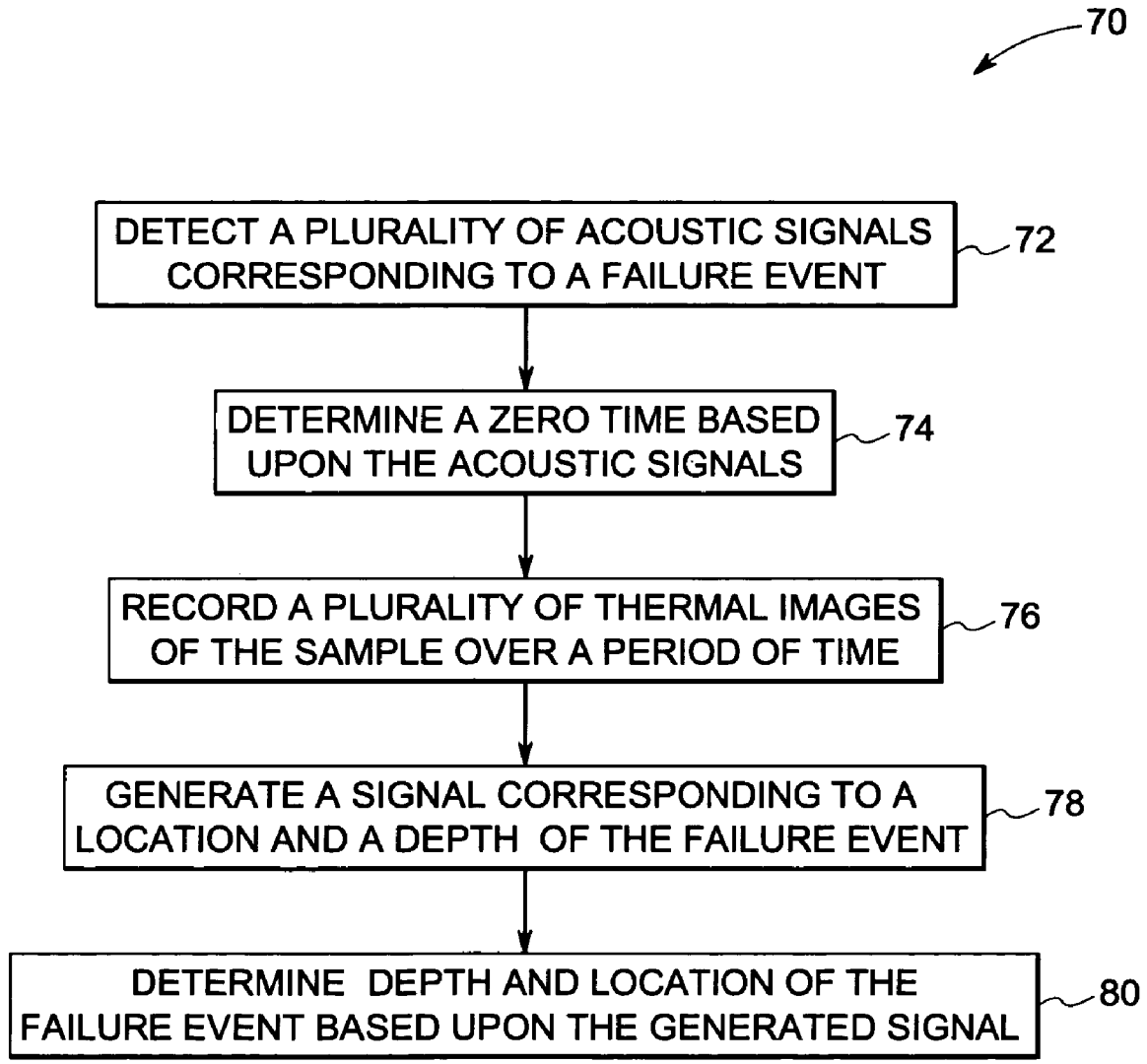
FIG. 4 is a flow chart illustrating exemplary steps for a method of detecting location and depth of a failure event in a sample.

FIG. 4 is a flow chart illustrating exemplary steps in a method 70 for detecting location and depth of a failure event in a sample. The method 70 includes detecting multiple acoustic signals corresponding to the failure event in step 72. In a particular embodiment, the detecting of multiple acoustic signals is performed in real time. A zero time is determined based upon the acoustic signals recorded in step 74. The zero time corresponds to a start time of occurrence of the failure event. The thermal energy is detected after a time lag at the surface of the sample via an infrared camera. Multiple thermal images of the sample are recorded over a period of time in step 76.

In a non-limiting example, the thermal images include thermal images of a resolution element on a surface of the sample. The recorded resolution element corresponds to a pixel. In a particular embodiment, the step 76 of recording the thermal images includes multiple steps beginning with determining individual pixel intensity for each of the pixels in each of the thermal images. The recording also includes determining mean pixel intensity for each thermal image. The recording further includes obtaining pixel contrast for each of the pixels of each of the thermal images subtracting the mean pixel intensity from the intensity of the individual pixel. A surface temperature-time pixel contrast curve is developed and a depth of the failure event is determined based upon the contrast curve. In an example, determining the depth of the failure event includes a determination based upon a heat flow relationship between an inflection point in the contrast curve and a heat-flow characteristic time. In a particular embodiment, the step 72 of detecting acoustic signals and the step 76 of recording thermal images are performed simultaneously. A signal such as a surface thermal profile and an acoustic emission profile of the sample corresponding to a location and a depth of the failure event may be generated in step 78. The method 70 also includes determining the depth and the location of the failure event from the generated signal in step 80.

EXAMPLES

The examples that follow are merely illustrative, and should not be construed to be any sort of limitation on the scope of the claimed invention.

Figure 5:
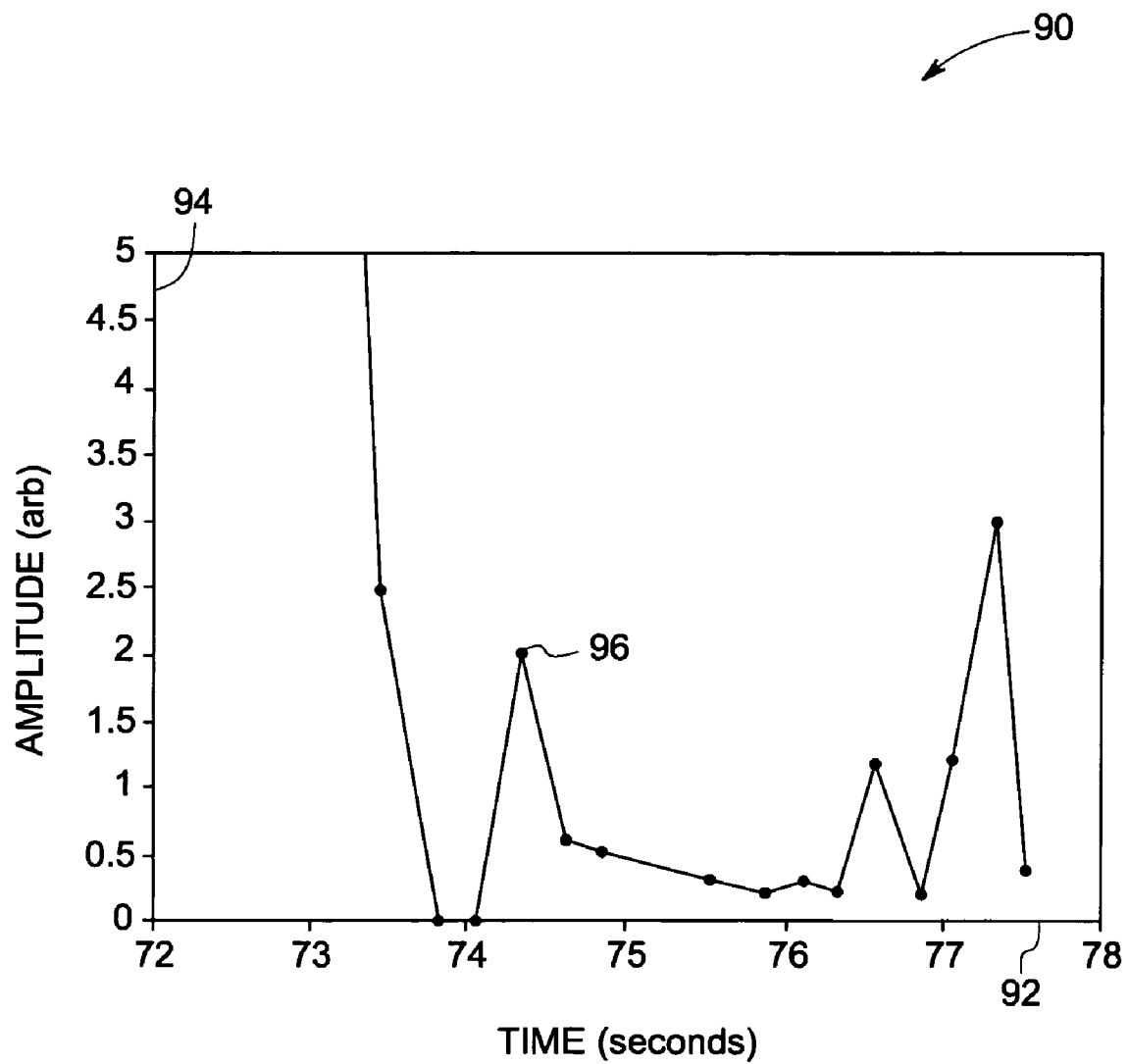
FIG. 5 is a graphical representation of acoustic emission signals corresponding to a failure event recorded over a period of time in a composite sample.

FIG. 5 is a graphical representation 90 of acoustic signals corresponding to a failure event recorded over a period of time in a composite sample as described in FIG. 3. The X-axis 92 represents time in seconds. The Y-axis 94 represents amplitude in arbitrary units. Each of the peaks 96 indicate a release of pulse of acoustic energy with varying amplitudes at about 74.5 seconds, about 76.5 seconds and about 77.2 seconds respectively. The peaks thus correspond to a new failure event at corresponding times of measurement.

Figure 6:
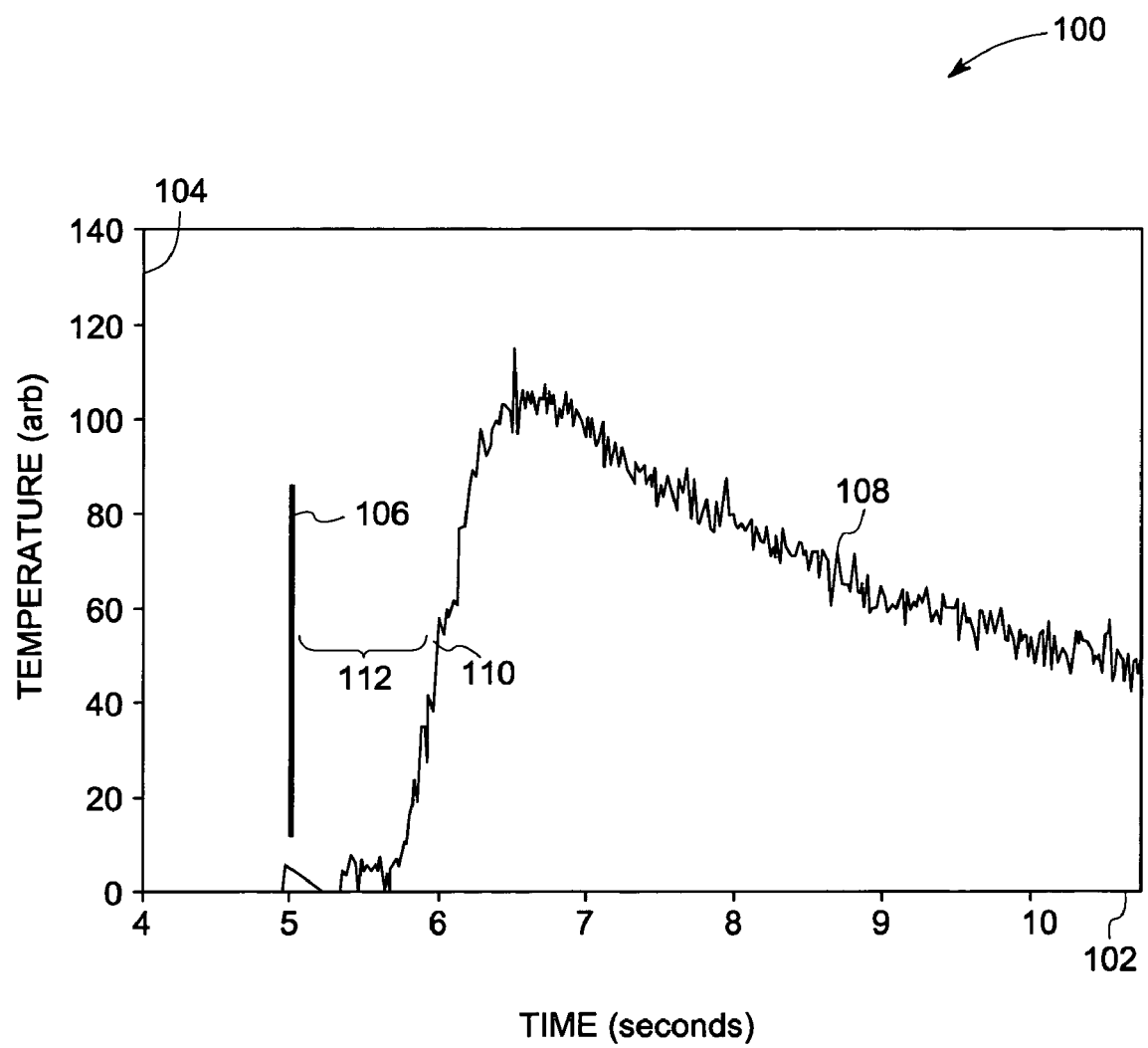
FIG. 6 is a graphical representation of a surface temperature-time profile of a composite sample being tested for a failure event.

FIG. 6 is a graphical representation 100 of a surface temperature-time profile of a sample as shown in FIG. 3. The X-axis 102 represents time in seconds. The Y-axis 104 represents temperature of the surface of the sample in arbitrary units. Line 106 represents an acoustic emission at about 5.5 seconds corresponding to a zero time of a failure event in the sample. Curve 108 represents thermal response of the surface measured simultaneously. It can be seen that the failure event occurs at about 5.5 seconds and can be detected at the surface via an infrared camera at an inflection point 110 that occurs at about 6.1 seconds. Thus, there is a time lag, referenced by 112, of about 0.6 second in the failure event being detected at the surface. Depth of the failure event can be obtained from a relationship between the time lag that is denoted by $t_{lag}$, and the depth 'd' given by:

$$t_{lag} = C \frac{d^2}{\pi^2 \alpha}; \quad (1)$$

wherein α is thermal diffusivity of the sample and C is a constant that varies in magnitude for a point failure event, a line failure event and a plane failure event respectively.

Beneficially, the above described system and method for locating failure events in samples are capable of determining location and depth of the failure events. Further, X-ray images captured by the above described X-ray detector may be correlated with surface thermal and acoustic emission profile obtained by the infrared imaging and acoustic emission sensing respectively to provide a complete description of failure evolution in the sample. Moreover, acoustic emission sensing enables detection of failure events as soon as it occurs in the sample and eliminates any time delay.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for locating a failure event in a sample, the system comprising:
    at least one sensor configured to detect acoustic energy corresponding to the failure event in the sample;
    an infrared camera configured to detect a thermal release of energy corresponding to the failure event in the sample; and
    a processor configured to determine a zero time of occurrence of the failure event based on the detected acoustic energy and to analyze the thermal release of energy detected after the zero time of occurrence to locate the failure event in the sample.

2. The system of claim 1, further comprising an X-ray source and a digital X-ray detector configured to capture an X-ray image of the sample, wherein the X-ray image is correlated with at least one of a plurality of acoustic data obtained with the sensor and a plurality of thermal data obtained with the infrared camera.

3. The system of claim 1, wherein the failure event comprises at least one of a point event, a line event or a plane event.

4. The system of claim 1, wherein the at least one sensor comprises a plurality of sensors.

5. The system of claim 1, wherein the at least one sensor comprises a transducer.

6. The system of claim 1, wherein the at least one sensor is further configured to detect a zero-time event, wherein the infrared camera records the thermal release of energy corresponding to the failure event in the sample in a plurality of frames, wherein the at least one sensor and the infrared camera are synchronized on a common time base, and wherein the processor is further configured to synchronize an event time detected by the sensor with a respective one of the frames.

7. The system of claim 1, wherein the infrared camera comprises a focal plane array of sensors.

8. The system of claim 1, wherein the sample comprises a plurality of plies oriented at angles in a range of about 0 degree to 180 degrees with respect to a longitudinal axis of the sample.

9. The system of claim 1, wherein the infrared camera is configured to operate at a frame rate within a range of about 50 frames per second to about 250 frames per second.

10. A method of detecting a failure event in a sample comprising:
    using at least one sensor to detect a plurality of acoustic signals corresponding to the failure event;
    determining a zero time based upon the acoustic signals;
    using an infrared camera to record a plurality of thermal images of the sample over a period of time;
    synchronizing the at least one sensor and the infrared camera on a common time base;
    generating a signal corresponding to a location and a depth of the failure event from the thermal images recorded on and after the zero time; and
    determining the depth and the location of the failure event based upon the generated signal.

11. The method of claim 10, wherein said using at least one sensor to detect and said using an infrared camera to record are performed simultaneously.

12. The method of claim 10, wherein the thermal images comprise thermal images of a resolution element on a surface of the sample, wherein each of the recorded resolution elements corresponds to a pixel, and wherein said using an infrared camera to record step further comprises:
   determining individual pixel intensity for each of the pixels in each of the thermal images;
   determining mean pixel intensity for each thermal image;
   obtaining pixel contrast for each of the pixels of each of the thermal images subtracting the mean pixel intensity from the intensity of the individual pixel;
   developing a surface temperature-time pixel contrast curve; and
   determining a depth of the failure event based upon the contrast curve.

13. The method of claim 10, wherein determining the depth of the failure event comprises a determination based upon a heat flow relationship between an inflection point in a contrast curve and a heat-flow characteristic time.

14. The method of claim 10, wherein said using at least one sensor to detect the plurality of acoustic signals step is performed in real time.

15. A system for locating a failure event in a sample comprising:
   at least one sensor configured to detect acoustic energy corresponding to the failure event in the sample;
   an infrared camera configured to detect a thermal release of energy corresponding to the failure event in the sample;
   an X-ray source configured to irradiate at least a portion of the sample; and
   a digital X-ray detector configured to capture at least one X-ray image of at least a portion of the sample; and
   a processor configured to determine a zero time of occurrence of the failure event based on the detected acoustic energy and to analyze the thermal release of energy detected after the zero time of occurrence to locate the failure event in the sample.

16. The system of claim 15, wherein the infrared camera comprises a focal plane array of sensors.

17. The system of claim 15, wherein the infrared camera comprises a frame rate with a range of about 50 frames per second to about 250 frames per second.

18. The system of claim 15, wherein the failure event comprises at least one of a point event, a line event or a plane event.

19. The system of claim 15, wherein the at least one sensor is further configured to detect a zero-time event, wherein the infrared camera records the thermal release of energy corresponding to the failure event in the sample in a plurality of frames, wherein the at least one sensor and the infrared camera are synchronized on a common time base, and wherein the processor is further configured to synchronize an event time detected by the sensor with a respective one of the frames.

20. The system of claim 15, further comprising means for correlating the X-ray image with at least one of a plurality of acoustic data obtained with the sensor and a plurality of thermal data obtained with the infrared camera.

* * * * *